United States Patent [19]

Collins et al.

[11] 4,021,771
[45] May 3, 1977

[54] SCAN ACOUSTICAL HOLOGRAPHIC IMAGING APPARATUS

[75] Inventors: H. Dale Collins; Edwin M. Sheen; R. Parks Gribble, all of Richland, Wash.

[73] Assignee: Holosonics, Inc., Richland, Wash.

[22] Filed: July 7, 1975

[21] Appl. No.: 593,450

[52] U.S. Cl. .............................. 340/5 H; 340/5 MP; 343/7.9

[51] Int. Cl.² .......................................... G01S 9/66

[58] Field of Search ......... 340/5 H, 5 MP; 343/7.9, 343/17

[56] References Cited

UNITED STATES PATENTS

| | | | |
|---|---|---|---|
| 3,715,482 | 2/1973 | Haines et al. | 340/5 H |
| 3,760,344 | 9/1973 | Hildebrand | 340/5 H |
| 3,792,423 | 2/1974 | Becker et al. | 340/5 MP |

Primary Examiner—Richard A. Farley
Attorney, Agent, or Firm—Wells, St. John & Roberts

[57] ABSTRACT

A scan acoustical holographic imaging apparatus is disclosed that is capable of displaying an isometric image of an object scanned with acoustical energy in which the image visually depicts surface contour information. The apparatus includes mechanisms for generating X, Y and Z electrical distance signals as an acoustical transducer is scanned in a scan plane over the object. The apparatus further includes mechanisms for generating object signals that are mixed with a holographic reference signal that may be phase shifted to produce a resultant holographic object signal which is used to modulate the brightness input of a CRT display device. The X, Y and Z electrical distance signals are transformed into an electronic isometric projection and applied to the horizontal and vertical inputs of the CRT display.

5 Claims, 4 Drawing Figures

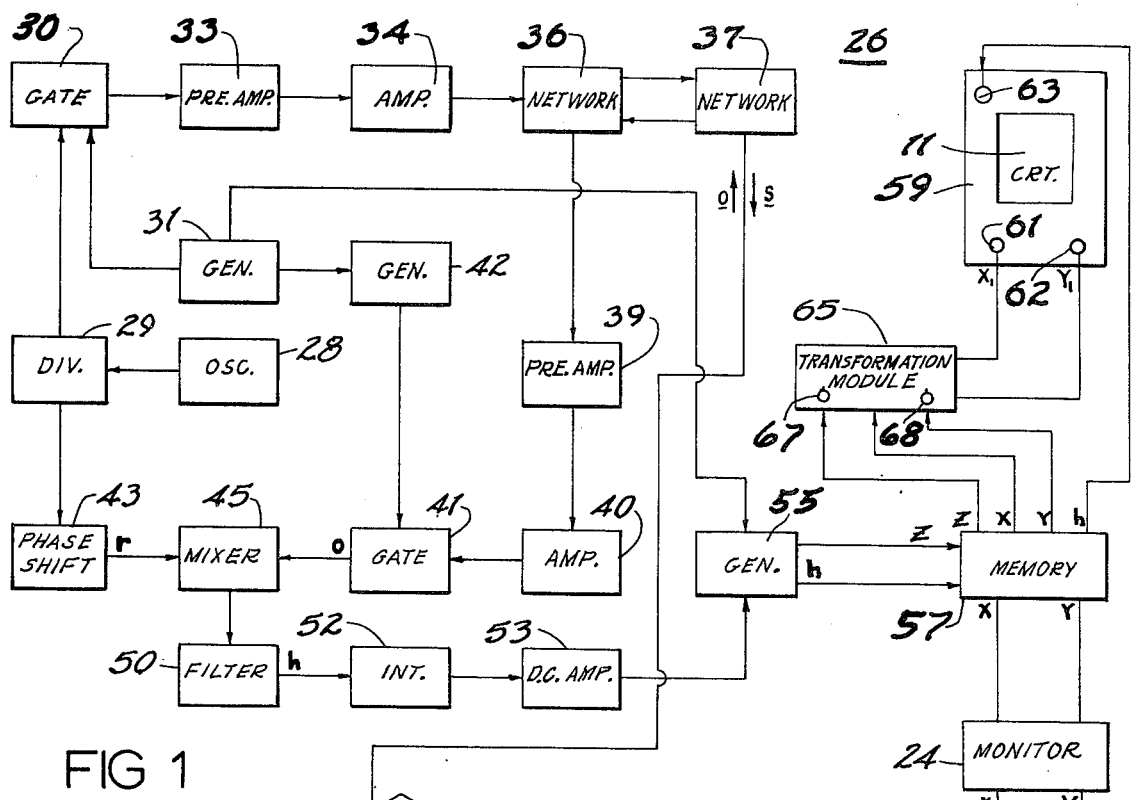
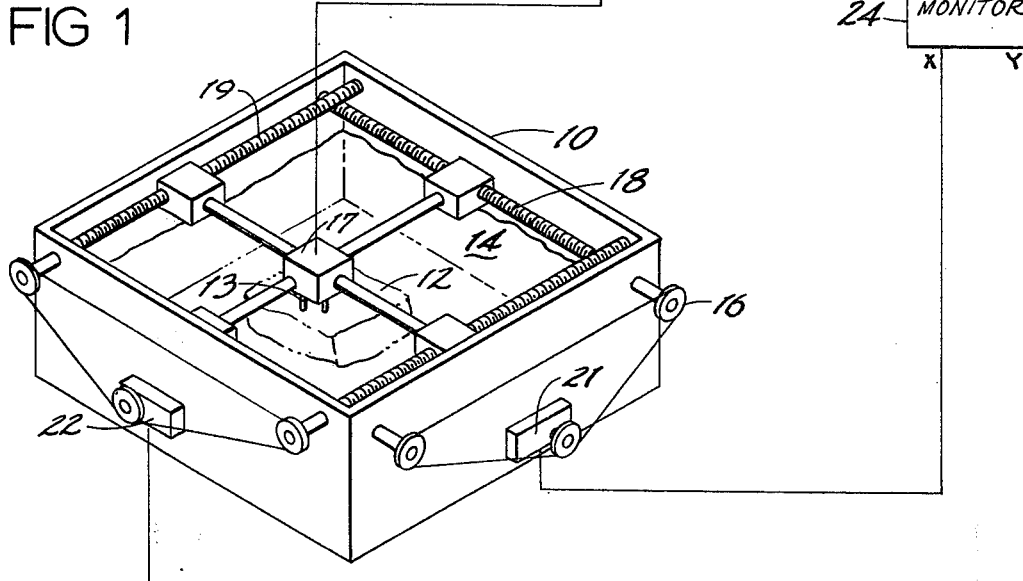
FIG 1
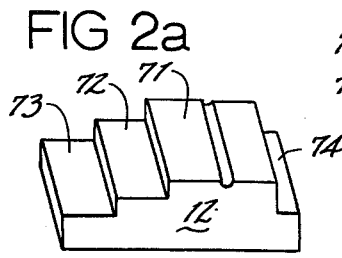
FIG 2a
FIG 2b (PRIOR ART)
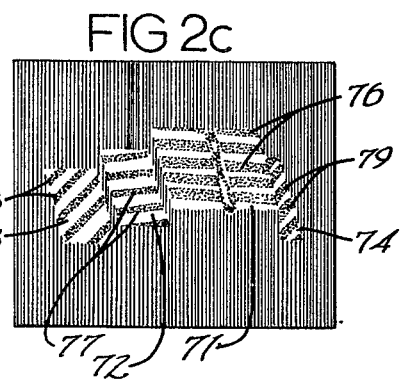
FIG 2c

SCAN ACOUSTICAL HOLOGRAPHIC IMAGING APPARATUS

BACKGROUND OF THE INVENTION

The present invention relates to techniques for presenting visual images of acoustically illuminated objects and more particularly to imaging techniques commonly referred to as B-scan, C-scan and scanned acoustical holography.

Such techniques are presently being utilized in varying degrees for medical diagnosis and for nondestructive testing of optically opaque materials (liquids and solids) in which an acoustical pulse transmitterreceiver is scanned over the material. Generally the images from B-scan and C-scan techniques are displayed on a cathode ray tube (CRT) in twodimensional form with B-scan display system showing a two dimensional depth cross section (X-Z plane or Y-Z plane) and the C-scan display system showing a two dimensional plan view (X-Y plane). In both systems the elapsed time of the acoustical pulse traveling from the transmitter to the attenuating surface or internal discontinuity back to the receiver and the amplitude of the reflected acoustical signal are measured. Generally the B-scan and C-scan techniques involved; (1) intensity modulation or brightening of the CRT spot in proportion to the amplitude of the reflected signal; (2) deflection of the CRT trace in synchronization of the scan mechanism over the object; (3) progressive production of the CRT image as the object is being scanned by use of long-persistent phosphor.

The visual image produced from both B and C-scan techniques is a flat two dimensional pattern which has the major shortcoming that both spatial and depth information are not displayed on a single record.

To overcome this shortcoming, Mssrs. Becker and Trantow devised a technique for displaying the scanned amplitude and lapsed time information in an isometric or three dimensional image of the object on a CRT. Such "isometric" technique is described in U.S. Pat. No. 3,792,423 granted Feb. 12, 1974. Although such technique is a significant improvement in the imaging of acoustically scanned objects, such images lack surface contouring information of the object or the internal defect and often have degraded surface definition.

One of the principal objects of this invention is to provide an imaging apparatus for visually displaying an isometric image of an acoustically illuminated object in which the isometric image depicts surface contour information and definition.

An additional object of this invention is to provide an improved isometric imaging system in which the view angle of the isometric image may be continuously varied while the image is being displayed with the image continuously depicting surface contour information of the object.

A further object of this invention is to provide a reliable acoustical imaging apparatus capable of providing flicker-free isometric images of objects illuminated with pulsed acoustical energy.

These and other objects and advantages of this invention will become apparent upon reading the following detailed description of a preferred embodiment.

BRIEF DESCRIPTION OF THE DRAWINGS

A preferred embodiment of this invention is illustrated in the accompanying drawing, in which:

FIG. 1 is an illustrative and schematic block diagram view of a preferred embodiment of this invention for displaying a visual image of an object that has been illuminated with acoustical energy in which the image depicts surface contouring information in the form of holographic fringe patterns; and FIGS. 2a, 2b, 2c are a sequence of isometric illustration views of a stepped object with; FIG. 2a illustrating an isometric view of the object itself, FIG. 2b illustrating an isometric image of the topographical stepped surfaces of the object being illuminated with acoustical energy utilizing the prior art "isometric" imaging technique described in the Becker et al U.S. Pat. No. 3,792,423; and FIG. 2c illustrating an isometric view of the topographical surfaces of the object depicting contour information of the surfaces in accordance with the present invention.

DETAILED DESCRIPTION OF A PREFERRED EMBODIMENT

Referring to the drawings in detail, there is illustrated in FIG. 1 a scan acoustical holographic imaging apparatus generally designated with the numeral 10 for generating and displaying an image 11 of an object 12 in which the object 12 is illuminated with pulsed acoustical energy from a scanned acoustical transducer 13.

The transducer 13 is acoustically coupled to the object 12 by a coupling liquid 14. Transducer 13 is moved in a scan plane (X-Y)over the object 12 by a scanning means 16. In this embodiment the scanning means includes a carriage 17 supporting the transducer 13 in which the carriage is moved in the X-Y scan plane by lead screws 18 and 19. Lead screws are operated by a X direction motor 21 and a Y direction motor 22. The position of the transducer at any particular time is monitored by a transducer position monitor 24 which generates X and Y electrical signals that are indicative of the position of the transducer in the X and Y scan plane at any particular moment.

The apparatus 10 includes an electrical circuit 26 for operating the transducer 13. The electrical circuit 26 includes an oscillator 28 for generating a wave train having a coherent frequency of between 0.25 – 20 MHz and preferably between 1–10 MHz. The wave train from the oscillator 28 is directd to a transmit gate 30 through a power divider 29. The transmit gate 30 is operated by transmit pulse generator 31 to gate the wave train and generate electrical pulse signals $s$ of predetermined repetition rate. Preferably the pulse width is between one-half and ten cycles per pulse and the pulse repetition rate is between 100 Hz and 1 kHz. Each pulse signal $s$ (pulse wave train) from the transmit gate is processed through a preamplifier 33 and a power amplifier 34. The pulse signal $s$ is directed through a signal decoupling decoding network 36 and a transducer impedance matching network 37 to the transducer 13. On receipt of the pulse signal $s$, the transducer generates an acoustical pulse having the same frequency, pulse repetition rate and pulse width as electrical signal s transmitted to the transducer. Echo acoustical pulse signals that are reflected from the object surface or interior discontinuities are received by the transducer 13 and converted to electrical signals o (short wave train) that are processed back through the impedance matching network 37 and the signal decoupling network 36 to a pre-amplifier 39 an amplifier 40 and transmitted to a receiving range gate 41. The range gate 41 is activated by a range or delay pulse generator 42 to transmit only those object signals that are received within a certain time frame in relation to the transmitted pulse. It may be desirable to set the range gate 41 to eliminate signals corresponding to reflections from surfaces or discontinuities outside the desired search volume. The acceptable object signals o are then transmitted to a multiplier or mixer network 45. At the multiplier 45 the object signal o is mixed with a reference electrical signal r to simulate an acoustical plane wave which is transmitted from the power divider 29 through a phase shifting device 43. Phase shifting device 43 has a variable phase control to adjust the phase shift of the reference signal with respect to the original signal to obtain a phase interference between the signal s and reference signal r. The reference signal may be varied in phase depending upon the desired reference angle with respect to the scan plane. If it is desired to utilize an "on-axis" holographic technique then the phase shift would be zero. Generally an off-axis technique is preferred in which the reference signal is adjusted in phase with respect to the signal s.

The multiplier 45 then generates a resultant interference signal which may be referred to as a holographic object signal h which is processed through a low pass filter 50, and integrator 52 and DC amplifier 53. The resultant holographic object signal h is then applied to a depth Z signal generator 55. The depth Z signal generator 55 is controlled by the transmit pulse generator 31 to activate a clock to determine the time interval between the transmission of the acoustical pulse s and the receipt of the reflected acoustical pulse. The time differential is indicative of the depth or Z dimension of the object from the scan plane at any particular X and Y coordinate position. The depth Z signal generator 55 then generates a Z or depth signal in addition to processing the holographic object signal h. The Z signal, the holographic object signal h, the X coordinate signal and Y coordinate signal are applied to a solid state digital memory device 57 for storage, as the signals are being generated. The solid state digital memory 57 has an output feature for supplying the signals to a display device generally designated with the numeral 59 which in a preferred embodiment is a CRT unit. The output of the digital memory 57 is synchoronized with the CRT unit so that the information is supplied at a rate compatible with the sweep rate of the CRT unit to prevent image flicker. The CRT unit includes an X' horizontal input 61 and a Y' vertical input 62 and a brightness or write input 63.

The apparatus 10 includes an isometric transformation module 65 for receiving the X, Y and Z signals from the memory 57 to transform such signals to an isometric electronic projection and then to pass the projection to the CRT unit through the X' and the Y' inputs 61 and 62. The isometric transformation module 65 converts the X, Y and Z signals to corresponding isometric X' horizontal signals and the Y' signals for the scope display. The transformation is accomplished according to the following formulas:

$$X' = X \cos \theta + Y \sin \theta \quad (1)$$

and $$Y' = (Y \cos \theta - X \sin \theta) \sin \phi + Z \cos \phi \quad (2)$$

where $\theta$ is the angle of rotation of the (X-Y) plane about the Z axis and $\phi$ is the tilt of the Z axis about the X' axis. Equation (1) and the terms inside the parenthesis of equation (2) correspond to a rotation of the object while the $\cos \phi$ and the Z $\sin \phi$ terms approximately modify the vertical perspective to correspond to the tilting of the object with respect to the Z axis to form an isometric view of the object. The X' and Y' signals are the applied to the X' and Y' input 61, 62 of the scope to provide the isometric image. The transformation module 65 includes a Z axis tilt control knob 67 for adjusting the angle $\phi$ and an X, Y plane knob 68 for adjusting the angle $\theta$. The tilt angle knob 67 and the X - Y plane angle knob 68 may be varied throughout 0°–90°. It should be noted that when the tilt angle $\phi$ is adjusted to 90° and angle $\theta$ is set at 0, the Z term is eliminated causing the iometric image to be condensed into a two dimensional C-scan image. Likewise when the knob 67 is adjusted with the angle $\phi$ equal to 0 and knob 68 is adjusted with angle $\theta$ equal to zero, then the isometric image condenses into a two dimensional B-scan image. Consequently the apparatus is capable of displaying isometric images at all angles between B-scan and C-scan.

The holographic object signal h is transmitted and applied to the brightness or write input 63 to modulate the brightness of the scope pattern image. The brightness modulation may be on-off, multilevel or analogue in nature.

In mathematical terms each echo or reflected acoustical signal returning to the transducer 13 is converted into electrical signals o which may be characterized by the expression:

$$B \cos [Wt + \phi_0 (X, Y)] \quad (3)$$

where B represents the amplitude of the signal W, t represents the time measured from an arbitrary beginning time and $\phi_0$ represents phase shifts induced in the signal by the object. Each reference signal r may be characterized by the expression:

$$C \cos [Wt + \phi_r (X,Y)] \quad (4)$$

where $\phi_r$ represents the phase shift of the reference signal with respect to the scan plane and C represents the amplitude of the reference signal r. The resultant holographic object signal h might be characterized by the expression:

$$D \cos [\phi_r (X,Y) - \phi_0 (X,Y)] \quad (5)$$

where D represent the amplitude of the holographic object signal h. This is a typical expression of a holographic recording. The phase angle $\phi_r$ of the reference wave may be expressed as:

$$\phi_r = \eta Y + \zeta Z \quad (6)$$

where $$\eta = (2\pi/\Lambda) \sin \psi \quad (7)$$

$$\zeta = (2\pi/\Lambda) \cos \psi \quad (8)$$

$\psi$ is the angle of incidence of the reference wave upon the scan plane and is the wavelength of the acoustic wave. The angle $\psi$ is controlled and is adjustable through the electrical phase shifter 43. The above equations assume that there is no tilt of the reference wave in the x-direction. This is not a restrictive assumption since the reference wave is a plane wave and is free to be oriented about the x-y axis to achieve the desired condition.

Also, in the reference wave, Z is related to Y through the equation:

$$Z = Y \tan \psi \quad (9)$$

By substitution the equation for $\phi_r$ becomes:

$$\phi_r = (2\pi/\Lambda)(2Y \sin \psi). \quad (10)$$

Now consider the phase $\phi_o$ of the waves reflected from the object.

$$\phi_o = (2\pi/\Lambda)(2NZ_o) \quad (11)$$

where $Z_o$ is the depth of the object from the scan plane and N is the number of reflections between the object and the scan plane. Often multiple reflections occur. The receiver gate 41 may be set to accept the Nth reflection. High order reflections yield greater accuracy in contouring unless the fringe density becomes so great that the individual fringe cannot be resolved.

The elevation $Z_o$ of the object surface is a function of $f(X,Y)$ of the $x$ and $y$ coordinates and is peculiar to the object. Thus, the brightness U of the contoured object surface corresponds to the holographic signal $h$ and may be characterized as:

$$U(X,Y) = D + D \cos[(2\pi/\Lambda)(2 Y \sin\psi - 2N f(X,Y)]. \quad (12)$$

This pattern of brightness is transformed by the transformation module 18 into the function $U(X', Y')$ in accordance with the transformation equations previously given.

FIG. 2a shows an object 12 having a plurality of stepped topographic surfaces 71, 72, 73 and 74. When the object is scanned utilizing the process outlined in the U.S. Pat. No. 3,792,423 granted Feb. 12, 1974, an isometric view 75 of the object 12 may be produced as illustrated in FIG. 2b in which the step surfaces 71-74 are substantially reproduced in the isometric image. It should be noted that the image does not depict contour information of the surfaces.

In contrast thereto, the image 76 (FIG. 2c) are produced by this invention in which the holographic object signals $h$ are applied to the brightness or write input 63 interferometric contouring fringe patterns 77-79 are produced providing contouring information of the stepped surfaces 71-74 respectively. It should be noted that the slope of surface 72 is slightly different than the slope of the surface 71. The surface 73 has a slope even greater than the slope of the surface 72 relative to surface 71. By use of the fringe patterns, it can be determined that surface 73 is tilted about 0.67° with respect to the scan plane, assuming an acoustical wavelength $\Lambda$ of 0.3 mm. in water. The step surface 73 has a width of approximately 19 mm. and a change of elevation across the width of about 0.22 mm. Likewise, the surface 74 shows a slope that is different from surface 71. The density of the fringe patterns indicate the degree of slope relative to the reference surface. Although the object 12 illustrates principally planar surfaces, the present invention is particularly useful in depicting the contour of curved surfaces and the degree of curvature.

It should be understood that the above described embodiment is simply illustrative of the principals of this invention and that numerous other embodiments may be readily devised without deviating therefrom. Therefore only the following claims are intended to define or restrict this invention.

What is claimed is:

1. A scan acoustical holographic imaging apparatus for visually displaying an isometric image of an object in which the image depicts measurable surface contour information of the object, comprising:
   an acoustical transducer for transmitting pulsed acoustical energy to the object of a preselected wavelength and for receiving echo pulsed acoustical energy from the object and generating an object electrical signal in response thereto;
   means for scanning the object with the transducer by moving the transducer over the object in a coordinate X-Y plane to generate a multitude of object signals containing object profile information;
   means for generating holographic reference electrical signals coherent with the object signal simulating a plane wave of irradiating acoustical energy having a reference plane and mixing the holographic reference signals with the multitude of object electrical signals to form resultant holographic object electrical signals containing profile and contour information of the object;
   means responsive to the time interval between the transmission of the pulsed acoustical energy and receipt of the echo pulsed acoustical energy by the transducer for generating a Z coordinate electrical signal indicative of the distance of the object from the X-Y coordinate scan plane;
   means responsive to the scanning means for generating X and Y coordinate electrical signals indicative of the position of the transducer as the object is being scanned;
   means responsive to the X, Y, and Z coordinate electrical signals and the holographic object electrical signals for electronically generating an isometric projection of the object containing holographic surface contour information; and
   means responsive to the electronic projection for visually displaying an isometric image of the object to form profile and contour lines showing measurable changes in contour of the object relative to the reference plane, said changes being measurable in terms of the wavelength of the pulsed acoustical energy.

2. The scan acoustical holographic imaging apparatus as defined in claim 1 wherein the means for electrically generating an isometric projection includes means for electronically varying the angular projection of the isometric projection.

3. The scan acoustical holographic imaging apparatus as defined in claim 1 wherein the means for electronically generating an isometric projection includes a solid state digital memory device for storing the X, Y and Z electrical signals and the holographic object electrical signals as the object is being scanned.

4. The scan acoustical holographic imaging apparatus as defined in claim 3 wherein said display means includes a cathode ray tube and wherein said solid state digital memory device has an output rate synchronized with the sweep rate of the cathode ray tube.

5. The scan acoustical holographic imaging apparatus as defined in claim 1 further comprising means for varying the phase of the holographic reference electrical signal to simulate varying the angle of the reference acoustical plane wave with respect to the scan plane.

* * * * *